United States Patent [19]
Firth et al.

[11] 4,057,996
[45] Nov. 15, 1977

[54] SYSTEMS FOR MONITORING THE COMPOSITION OF EXHAUST GASES

[75] Inventors: Jack Graham Firth, St Albans; Thomas Alwyn Jones, Dronfield, near Sheffield; Brenda Rimmington, Sheffield, all of England

[73] Assignee: National Research Development Corporation, London, England

[21] Appl. No.: 647,983

[22] Filed: Jan. 8, 1976

[30] Foreign Application Priority Data

Jan. 17, 1975 United Kingdom ............... 02130/75

[51] Int. Cl.² ........................................... G01N 27/12
[52] U.S. Cl. ........................................... 73/23; 338/34
[58] Field of Search ............... 73/23, 27 R; 338/34, 338/35; 340/237 R; 324/71 SN; 23/232 E, 254 E

[56] References Cited

U.S. PATENT DOCUMENTS

| 3,751,968 | 8/1973 | Loh et al. | 73/23 |
| 3,865,550 | 2/1975 | Bott et al. | 73/23 |
| 3,879,985 | 4/1975 | Maslen | 73/27 R |
| 3,932,246 | 1/1976 | Stadler et al. | 73/27 R |
| 3,936,794 | 2/1976 | Beaudoin et al. | 73/23 |
| 3,953,173 | 4/1976 | Obayashi et al. | 73/27 R |

Primary Examiner—Jerry W. Myracle
Assistant Examiner—Stephen A. Kreitman
Attorney, Agent, or Firm—Cushman, Darby & Cushman

[57] ABSTRACT

In a system for monitoring the composition of exhaust gases from an internal combustion engine, a gas-sensitive resistor consisting of gallium oxide is exposed to the gases and is maintained at a substantially constant temperature above that of the gases. A signal is generated dependent on the resistance of the resistor, which varies monotonically with the air/fuel ratio of the inlet mixture, this signal being usable in a system for automatically controlling the composition of the inlet mixture.

5 Claims, 5 Drawing Figures

SYSTEMS FOR MONITORING THE COMPOSITION OF EXHAUST GASES

This invention relates to systems for monitoring the composition of exhaust gases emitted from an apparatus for the controlled combustion of carbonaceous fuel.

A particular requirement for such systems arises in connection with the desire to provide a means for automatically controlling the composition of the fuel-air mixture fed to an internal combustion engine in such a way as to minimize fuel consumption and the emission of pollutant gases such as carbon monoxide. For effective operation in this case, the monitoring system must be capable of responding to variations of the concentration of oxygen and/or reducing gases in exhaust gas mixtures corresponding to a wide range of fuel-air mixtures lying on both sides of the stoichiometric ratio of air to fuel for complete oxidation, and especially variations in exhaust gas mixtures corresponding to "lean" fuel-air mixtures (i.e. those containing a lower proportion of fuel than that corresponding to the stoichiometric ratio). A particularly important practical consideration is that the monitoring system should employ a transducer which exhibits a monotonic change in a measurable parameter over the relevant range of exhaust gas compositions; for compositions corresponding to "rich" inlet mixtures the transducer will be responding mainly to changes in the concentration of reducing gases in the exhaust gas mixture, while for compositions corresponding to "lean" inlet mixtures the transducer will be responding mainly to changes in the concentration of oxygen in the exhaust gas mixture. The foregoing considerations apply to all types of internal combustion engine, and similar considerations apply in the case of other types of combustion apparatus (such as furnaces) where it may be desired to control the composition of the inlet mixture of fuel and air (or other oxygen-containing component) in response to changes in the composition of the exhaust gases emitted from the apparatus.

It is well known that the electrical conductivities of many semiconducting metal oxides are sensitive to the concentrations of oxidising and/or reducing gases in the atmospheres above their surfaces, and that gas-sensitive resistors consisting of some such oxides are capable of satisfactory operation at relatively high temperatures. Attention has therefore been directed to the possibility that such resistors would be suitable for use as transducers in monitoring systems of the kind discussed above; for example reference may be made to British Patent Specification No. 1,376,769, which particularly mentions the use in this context of transition metal oxides and rare earth metal oxides.

The present invention is based on the discovery that, in exploiting the possibility just referred to, particularly satisfactory results can be achieved by the use of gas-sensitive resistors consisting essentially of gallium oxide ($Ga_2O_3$). The conductivities of semiconducting metal oxides of course vary appreciably with temperature, and it will therefore be appreciated that, when using a gallium oxide gas-sensitive resistor in a monitoring system of the kind referred to, the resistor must be maintained at a substantially constant temperature if the system is to operate consistently. Since this temperature must be above that of the exhaust gases to which the resistor is exposed, provision must be made for an independent supply of heat to the resistor.

According to one aspect of the invention, therefore, there is provided a system for monitoring the composition of exhaust gases emitted from an apparatus for the controlled combustion of carbonaceous fuel, the system comprising a gas-sensitive resistor consisting essentially of gallium oxide and mounted so as to be exposed to the exhaust gases in operation of the apparatus, means for maintaining the resistor at a substantially constant temperature above that of the exhaust gases to which the resistor is exposed, and means for generating a signal dependent on the resistance of the resistor.

According to another aspect of the invention, a device for use in such a system comprises a gas-sensitive resistor consisting essentially of gallium oxide exposed for contact with a gaseous environment, and an electric resistance heater closely juxtaposed with the gas-sensitive resistor and operable to heat it to a temperature of at least 900° C.

The invention will be further described and explained with reference to the accompanying drawings, in which.

Figure 1:
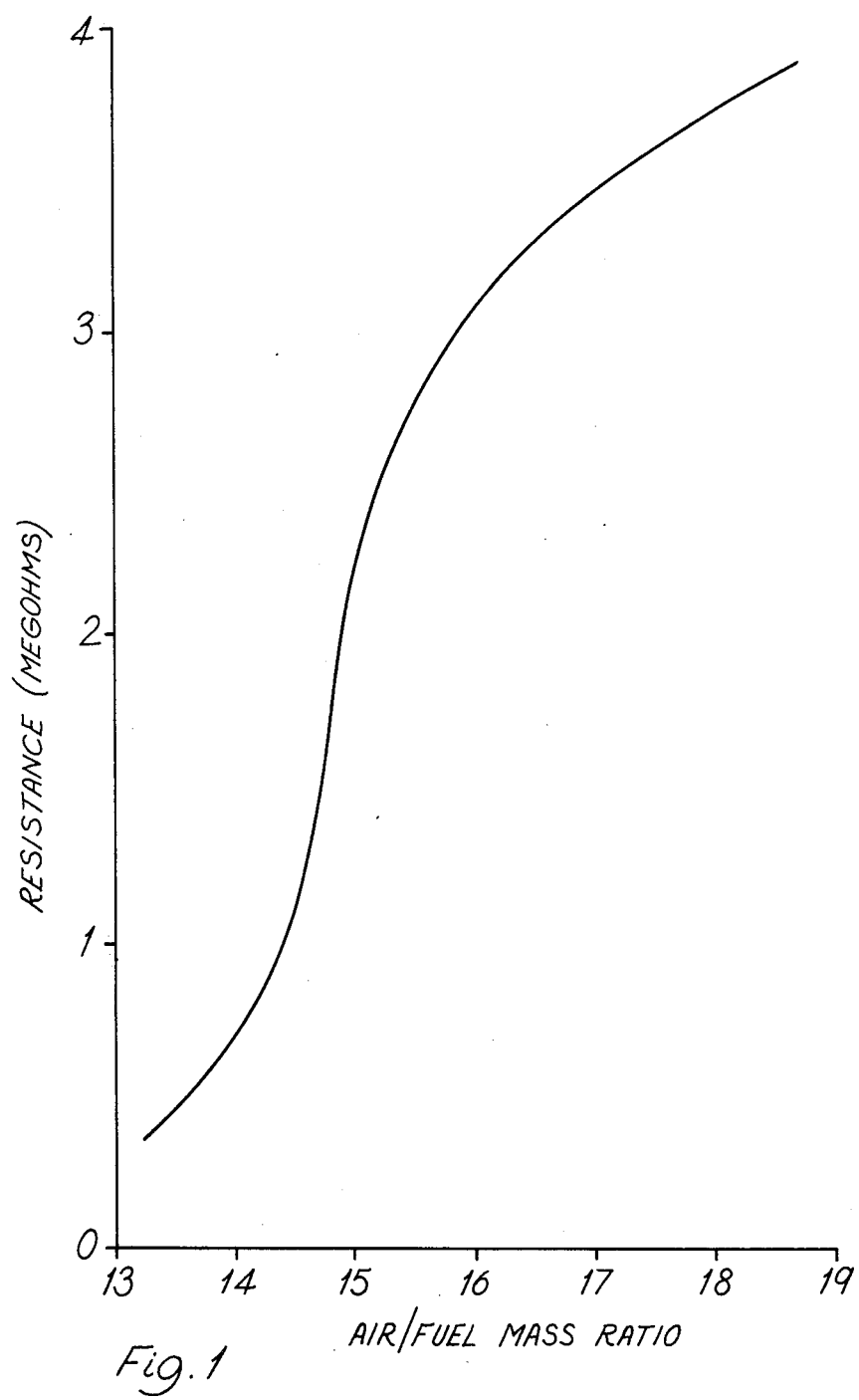
FIG. 1 is an explanatory diagram.

The results obtainable by using a monitoring system according to the invention may be illustrated by reference to FIG. 1, which shows how the resistance (expressed in megohms) of a typical gallium oxide gas-sensitive resistor, mounted in the exhaust system of a conventional petrol engine and maintained at a temperature of 900° C, varies as the air to fuel mass ratio of the inlet mixture is varied; it should be noted that the stoichiometric ratio has a value of 15, and that it will normally be desired to operate the engine with an air to fuel ratio in the range 15.5 to 17. The behaviour of gallium oxide in this respect is in distinct contrast to that of other refractory metal oxides which have been investigated, e.g. titanium dioxide, vanadium pentoxide, chromium oxide and cerium oxide; under similar conditions to those indicated above, gas-sensitive resistors using these other oxides exhibit a "switch-type" characteristic in which there is a stepwise change in resistance (in some cases of several orders of magnitude) at or near the stoichiometric ratio but only slight changes in resistance for variation in the composition of the inlet mixture on either side of this ratio. Such a characteristic is of course ill-adapted for use where it is required to provide for fine adjustment of the composition of the inlet mixture, especially in the important range of "lean" mixtures.

Further relevant factors are that: gallium oxide exhibits a rapid response to changes in gas concentration (with a time lag much shorter than one second); it is stable when exposed to both reducing and oxidising exhaust gas composition at temperatures up to at least 900° C, so that it can be disposed close to the combustion region of an apparatus whose exhaust gases are to be monitored (as is desirable to ensure rapid response to changes in the inlet conditions); it shows negligible change in characteristics when repeatedly cycled between elevated operating temperatures and atmospheric temperatures; it can be readily deposited in a mechanically strong form, thus enabling the fabrication of gas-sensitive resistors to be economically effected.

Certain embodiments of the invention will now be described by way of example with reference to FIGS. 2 to 5 of the accompanying drawings.

Figure 2:
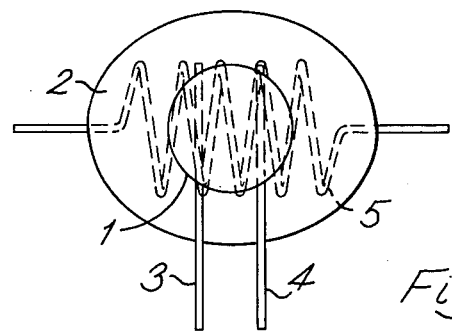
FIG. 2 is a view of a gas-sensitive device.

The device shown in FIG. 2 incorporates a gas-sensitive resistor 1 in the form of a film of gallium oxide deposited on the surface of a fused glass bead 2 which is of approximately spherical shape of diameter 1 mm., the resistor 1 being provided with leads 3 and 4 constituted by wires partly embedded in the bead 2; since the device is required to operate at temperatures of the order of 900° C, the glass of the bead 2 is of a high-melting type having a softening point of about 1200° C. The device further incorporates an electric resistance heater 5 constituted by a length of platinum-rhodium wire the central part of which is in the form of a coil embedded in the bead 2, the heater 5 typically having a resistance of the order of a few ohms at the operating temperature of the device; it is significant to note here that the heater 5 has an appreciable temperature coefficient of resistance. In manufacture of the device, the resistor 1 may conveniently be formed by applying an aqueous slurry of gallium oxide to the surface of the bead 2 and then heating the bead 2 to a temperature of about 500° C by means of the heater 5 so as to form a cohesive and adherent film of gallium oxide; the slurry may suitably be prepared by grinding gallium oxide to an average particle size of 20 microns and then mixing the ground oxide with an equal weight of water.

Figure 3:
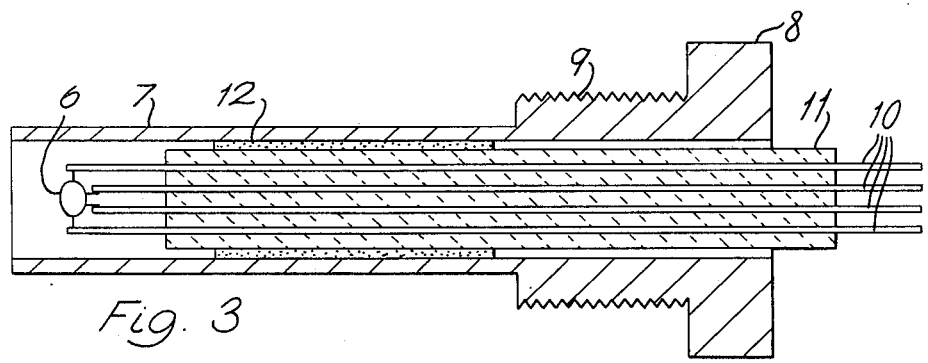
FIG. 3 is a sectional view of a sensing head incorporating a device as shown in FIG. 2.
Figure 4:
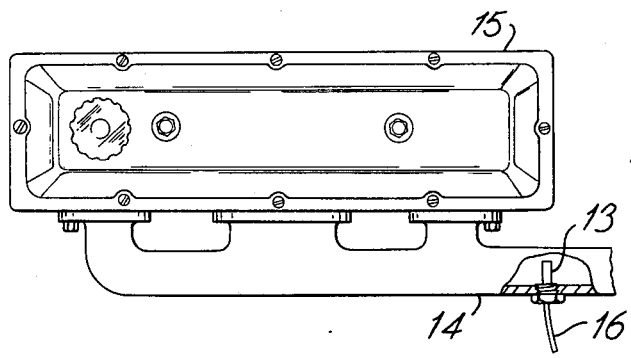
FIG. 4 is a diagrammatic view, partly in section, of part of a conventional internal combustion engine equipped with a sensing head as shown in FIG. 3.

For use in monitoring the composition of exhaust gases emitted by an internal combustion engine, the device shown in FIG. 2 is mounted in a sensing head of the form shown in FIG. 3. In this sensing head the gas-sensitive device 6 is disposed within one end of a metal sleeve 7 which is formed with a flange 8 and a threaded portion 9 adjacent its other end. The device 6 is supported by virtue of the leads 3 and 4 and the ends of the heater 5 being attached to four wires 10 which pass through separate bores in a ceramic plug 11, the plug 11 being secured within the sleeve 7 by means of a layer 12 of a heat-resistance adhesive. FIG. 4 illustrates diagrammatically a conventional internal combustion engine equipped with a sensing head 13 of the form shown in FIG. 3, the head 13 being mounted in the exhaust system 14 of the engine at a position close to the cylinder block 15 and electrical connection to the head 13 being made by means of a four-core cable 16; it will be appreciated that the device 6 in the head 13 is shielded from the direct influence of the flow of the exhaust gases by the sleeve 7. The temperature of the exhaust gases at the position of the head 13 in normal operation of the engine is of the order of 700° C, and accordingly the device 6 is arranged to be operated at a temperature of about 900° C.

Figure 5:
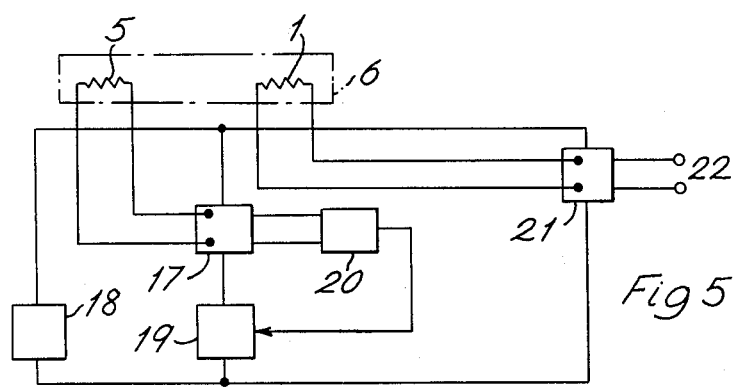
FIG. 5 is a diagram illustrating the electrical circuit of a monitoring system associated with the engine shown in FIG. 4.

As illustrated in FIG. 5, for this purpose the heater 5 of the device 6 is connected in one arm of a Wheatstone bridge circuit 17 (indicated only diagrammatically since it is of conventional form), the circuit 17 being supplied with current from a source 18 of nominally constant voltage via an electrically controllable impedance device 19 (which may suitably be a power transistor). The components of the circuit 17 (all of which are of relatively low resistance) are chosen so that the circuit 17 is substantially balanced when the resistance of the heater 5 has a value corresponding to the desired operating temperature of the device 6. Any out-of-balance voltage from the circuit 17 is applied to a differential amplifier 20, the output of which is utilised to control the device 19 in a sense such as to tend to restore the balance of the circuit 17. There is thus provided a servo loop which functions to control the current supplied to the circuit 17 in such a manner as to maintain the resistance of the heater 5 substantially constant at the value which it has at the desired operating temperature. It should be noted that this arrangement is in accordance with the principles disclosed in U.S. Pat. No. 3,932,807 by Ronald Wilson.

The resistor 1 of the device 6 is connected in a conventional resistance measuring circuit 21 (for example a Wheatstone bridge circuit) which is also supplied with current from the source 18, the circuit 21 having output terminals 22 between which appears a voltage dependent on the value of the resistor 1 and hence on the composition of the air-fuel mixture being fed to the engine. The signal constituted by this voltage may suitably be used to control a servo mechanism (not shown) which is operative to adjust automatically the setting of the carburettor or like device (not shown) associated with the engine so as to maintain a desired composition of the inlet mixture. In view of the high value of the resistance of the resistor 1 (typically of the order of a few megohms at a temperature of 900° C when the air to fuel ratio of the inlet mixture is stoichiometric), the current taken by the circuit 21 from the source 18 will of course be much lower than that taken by the circuit 17.

We claim:

1. A system for monitoring the composition of exhaust gases emitted from an apparatus for the controlled combustion of carbonaceous fuel, the system comprising:
    a gas-sensitive resistor consisting essentially of gallium oxide;
    means mounting said resistor for exposure to the exhaust gases in operation of the apparatus;
    means for maintaining said resistor at a substantially constant temperature above that of the exhaust gases to which said resistor is exposed; and
    means for generating a signal dependent on the resistance of said resistor.

2. A system according to claim 1, in which said means for maintaining said resistor at a substantially constant temperature comprises:
    an electric resistance heater closely juxtaposed with said resistor and operable to heat it to said temperature, said heater having an appreciable temperature coefficient of resistance;
    means for supplying a variable current to said heater;
    means for sensing variations in the resistance of said heater; and
    means for automatically controlling the operation of said current supplying means in accordance with the operation of said sensing means to maintain the resistance of said heater substantially constant at a value corresponding to said temperature.

3. A system according to claim 2, in which said resistor is constituted by a film of gallium oxide adhering to the surface of a fused glass bead, and said heater is constituted by a length of wire the central part of which is in the form of a coil embedded in said bead.

4. A device for use in a system for monitoring the composition of exhaust gases emitted from an apparatus for the controlled combustion of carbonaceous fuel, the device comprising:

a gas-sensitive resistor consisting essentially of gallium oxide exposed for contact with a gaseous environment; and an electric resistance heater closely juxtaposed with said resistor and operable to heat it to a temperature of at least 900° C.

5. A device according to claim 4, in which said resistor is constituted by a film of gallium oxide adhering to the surface of a fused glass bead, and said heater is constituted by a length of wire the central part of which is in the form of a coil embedded in said bead.

* * * * *